(12) United States Patent
Russell et al.

(10) Patent No.: US 10,617,510 B2
(45) Date of Patent: *Apr. 14, 2020

(54) INTRODUCER SHEATH WITH EMBOLIC PROTECTION

(71) Applicant: Emboline, Inc., Santa Cruz, CA (US)

(72) Inventors: Scott Russell, San Jose, CA (US); Amir Belson, Saryou (IL)

(73) Assignee: Emboline, Inc., Santa Cruz, CA (US)

(*) Notice: Subject to any disclaimer, the term of this patent is extended or adjusted under 35 U.S.C. 154(b) by 243 days.

This patent is subject to a terminal disclaimer.

(21) Appl. No.: 15/848,762

(22) Filed: Dec. 20, 2017

(65) Prior Publication Data

US 2018/0110607 A1   Apr. 26, 2018

Related U.S. Application Data

(63) Continuation of application No. 14/537,814, filed on Nov. 10, 2014, now Pat. No. 9,877,821.

(60) Provisional application No. 62/050,156, filed on Sep. 14, 2014.

(51) Int. Cl.
| | |
|---|---|
| *A61F 2/01* | (2006.01) |
| *A61F 2/24* | (2006.01) |
| *A47C 19/02* | (2006.01) |
| *A47C 19/12* | (2006.01) |

(52) U.S. Cl.
CPC .............. *A61F 2/013* (2013.01); *A47C 19/02* (2013.01); *A47C 19/12* (2013.01); *A61F 2/2427* (2013.01); *A61F 2002/011* (2013.01); *A61F 2002/015* (2013.01); *A61F 2002/016* (2013.01); *A61F 2002/018* (2013.01); *A61F 2230/008* (2013.01); *A61F 2230/0067* (2013.01); *A61F 2230/0069* (2013.01)

(58) Field of Classification Search
CPC .......... A61F 2002/018; A61F 2002/016; A61F 2002/015; A61F 2002/011; A61F 2/013
See application file for complete search history.

(56) References Cited

U.S. PATENT DOCUMENTS

| | | | |
|---|---|---|---|
| 4,723,549 A | 2/1988 | Wholey et al. | |
| 4,790,809 A | 12/1988 | Kuntz | |
| 5,108,419 A | 4/1992 | Reger et al. | |
| 5,197,485 A | 3/1993 | Grooters | |
| 5,769,816 A | 6/1998 | Barbut et al. | |
| 5,769,819 A | 6/1998 | Schwab et al. | |

(Continued)

FOREIGN PATENT DOCUMENTS

| | | |
|---|---|---|
| CA | 2609800 A1 | 1/2007 |
| CN | 101351242 A | 1/2009 |

(Continued)

OTHER PUBLICATIONS

US 6,348,062 B1, 02/2002, Hopkins et al. (withdrawn)

(Continued)

*Primary Examiner* — Diane D Yabut
(74) *Attorney, Agent, or Firm* — Wilson Sonsini Goodrich & Rosati

(57) ABSTRACT

The embolic protection device comprises an embolic filter attached to an inner sheath. The embolic filter includes at least a first catheter access port and a second catheter port. At least the first catheter port will typically be radially expandable to receive catheters of different diameters and will be located at an atypical end of an aero conical structure at a downstream end of the filter.

20 Claims, 9 Drawing Sheets

(56) References Cited

U.S. PATENT DOCUMENTS

| | | |
|---|---|---|
| 5,797,880 A | 8/1998 | Erskine |
| 5,800,525 A | 9/1998 | Bachinski et al. |
| 5,807,327 A | 9/1998 | Green et al. |
| 6,013,051 A | 1/2000 | Nelson |
| 6,083,239 A | 7/2000 | Addis |
| 6,117,154 A | 9/2000 | Barbut et al. |
| 6,120,534 A | 9/2000 | Ruiz |
| 6,139,517 A | 10/2000 | Macoviak et al. |
| 6,152,144 A | 11/2000 | Lesh et al. |
| 6,245,012 B1 | 6/2001 | Kleshinski |
| 6,254,563 B1 | 7/2001 | Macoviak et al. |
| 6,254,633 B1 | 7/2001 | Pinchuk et al. |
| 6,258,120 B1 | 7/2001 | McKenzie et al. |
| 6,348,063 B1 | 2/2002 | Yassour et al. |
| 6,355,051 B1 | 3/2002 | Sisskind et al. |
| 6,361,545 B1 | 3/2002 | Macoviak et al. |
| 6,371,935 B1 | 4/2002 | Macoviak et al. |
| 6,461,370 B1 | 10/2002 | Gray et al. |
| 6,499,487 B1 | 12/2002 | McKenzie et al. |
| 6,537,297 B2 | 3/2003 | Tsugita et al. |
| 6,547,760 B1 | 4/2003 | Samson et al. |
| 6,682,543 B2 | 1/2004 | Barbut et al. |
| 6,692,513 B2 | 2/2004 | Streeter et al. |
| 6,695,864 B2 | 2/2004 | Macoviak et al. |
| 6,709,415 B2 | 3/2004 | Navia et al. |
| 6,712,834 B2 | 3/2004 | Yassour et al. |
| 6,746,469 B2 | 6/2004 | Mouw |
| 6,808,520 B1 | 10/2004 | Fourkas et al. |
| 7,044,958 B2 | 5/2006 | Douk et al. |
| 7,232,453 B2 | 6/2007 | Shimon |
| 7,235,060 B2 | 6/2007 | Kraus |
| 7,537,600 B2 | 5/2009 | Eskuri et al. |
| 7,758,606 B2 | 7/2010 | Streeter et al. |
| 7,766,932 B2 | 8/2010 | Melzer et al. |
| 8,052,717 B2 | 11/2011 | Mujkanovic et al. |
| 8,114,114 B2 | 2/2012 | Belson |
| 8,123,779 B2 | 2/2012 | Demond et al. |
| 8,298,258 B2 | 10/2012 | Anderson et al. |
| 8,308,754 B2 | 11/2012 | Belson |
| 8,337,519 B2 | 12/2012 | Wasicek et al. |
| 8,382,788 B2 | 2/2013 | Galdonik et al. |
| 8,414,482 B2 | 4/2013 | Belson |
| 8,420,902 B2 | 4/2013 | Gilsinger et al. |
| 8,430,904 B2 | 4/2013 | Belson |
| 8,679,149 B2 | 3/2014 | Belson |
| 8,728,114 B2 | 5/2014 | Belson |
| 8,740,930 B2 | 6/2014 | Goodwin et al. |
| 8,968,354 B2 | 3/2015 | Wang et al. |
| 9,107,734 B2 | 8/2015 | Belson |
| 9,144,485 B2 | 9/2015 | Bergheim et al. |
| 9,492,265 B2 | 11/2016 | Russell et al. |
| 9,744,023 B2 | 8/2017 | Wang et al. |
| 9,827,085 B2 | 11/2017 | Russell et al. |
| 9,877,821 B2 | 1/2018 | Russell et al. |
| 2001/0044632 A1 | 11/2001 | Daniel et al. |
| 2002/0004667 A1 | 1/2002 | Adams et al. |
| 2002/0058964 A1 | 5/2002 | Addis |
| 2002/0128680 A1 | 9/2002 | Pavlovic |
| 2003/0040736 A1 | 2/2003 | Stevens et al. |
| 2003/0100940 A1 | 5/2003 | Yodfat |
| 2003/0171803 A1 | 9/2003 | Shimon |
| 2004/0034380 A1 | 2/2004 | Woolfson et al. |
| 2004/0073253 A1 | 4/2004 | Morrill et al. |
| 2004/0138692 A1 | 7/2004 | Phung et al. |
| 2004/0215167 A1 | 10/2004 | Belson |
| 2004/0225354 A1 | 11/2004 | Allen et al. |
| 2005/0010246 A1 | 1/2005 | Streeter et al. |
| 2005/0137696 A1 | 6/2005 | Salahieh et al. |
| 2005/0283186 A1 | 12/2005 | Berrada et al. |
| 2006/0287668 A1 | 12/2006 | Fawzi et al. |
| 2006/0293706 A1 | 12/2006 | Shimon |
| 2007/0027534 A1 | 2/2007 | Bergheim et al. |
| 2007/0060944 A1 | 3/2007 | Boldenow et al. |
| 2007/0073246 A1 | 3/2007 | Simon |
| 2007/0073332 A1 | 3/2007 | Miller et al. |
| 2008/0027481 A1 | 1/2008 | Gilson et al. |
| 2009/0149881 A1 | 6/2009 | Vale et al. |
| 2010/0010535 A1 | 1/2010 | Mujkanovic et al. |
| 2010/0274277 A1 | 10/2010 | Eaton |
| 2010/0312268 A1 | 12/2010 | Belson |
| 2012/0016408 A1 | 1/2012 | Barbut et al. |
| 2012/0109182 A1 | 5/2012 | Belson |
| 2012/0109183 A1 | 5/2012 | Belson |
| 2012/0271340 A1 | 10/2012 | Castellano et al. |
| 2013/0035716 A1 | 2/2013 | Belson |
| 2013/0035717 A1 | 2/2013 | Belson |
| 2013/0096606 A1 | 4/2013 | Bruchman et al. |
| 2013/0178891 A1 | 7/2013 | Russell et al. |
| 2013/0238011 A1 | 9/2013 | Belson |
| 2013/0245669 A1 | 9/2013 | Basu et al. |
| 2013/0267993 A1 | 10/2013 | Carpenter et al. |
| 2014/0000091 A1 | 1/2014 | Angel et al. |
| 2014/0058372 A1 | 2/2014 | Belson |
| 2014/0155929 A1 | 6/2014 | Belson |
| 2014/0214069 A1 | 7/2014 | Franklin et al. |
| 2014/0249568 A1 | 9/2014 | Adams et al. |
| 2015/0066075 A1 | 3/2015 | Russell et al. |
| 2015/0320540 A1 | 11/2015 | Belson |
| 2015/0366650 A1 | 12/2015 | Zi et al. |
| 2016/0317277 A1 | 11/2016 | Carpenter et al. |
| 2018/0206970 A1 | 7/2018 | Eggert et al. |
| 2019/0015152 A1 | 1/2019 | Howard et al. |

FOREIGN PATENT DOCUMENTS

| | | |
|---|---|---|
| CN | 102256566 A | 11/2011 |
| CN | 102973332 A | 3/2013 |
| JP | H09276414 A | 10/1997 |
| JP | 2007527264 A | 9/2007 |
| WO | WO-03094791 A2 | 11/2003 |
| WO | WO-2004019817 A1 | 3/2004 |
| WO | WO-2004021922 A2 | 3/2004 |
| WO | WO-2006138391 A2 | 12/2006 |
| WO | WO-2009038799 A1 | 3/2009 |
| WO | WO-2013103979 A1 | 7/2013 |
| WO | WO-2016040923 A2 | 3/2016 |
| WO | WO-2016040923 A3 | 8/2016 |
| WO | WO2017116828 | 7/2017 |

OTHER PUBLICATIONS

International search report and written opinion dated May 5, 2017 for PCT Application No. PCT/US2016/067686.

"IPRP for PCT/US2016/067686 Jul. 3, 2018".

Notice of allowance dated Jul. 14, 2016 for U.S. Appl. No. 13/735,864.

Notice of allowance dated Sep. 1, 2017 for U.S. Appl. No. 15/335,322.

Office action dated Feb. 9, 2017 for U.S. Appl. No. 15/335,322.

European search report and search opinion dated Apr. 17, 2015 for EP Application No. 13733627.7.

International search report and written opinion dated Apr. 9, 2008 for PCT/US2007/024558.

International search report and written opinion dated Apr. 22, 2013 for PCT Application No. US2013/20563.

"International search report and written opinion dated Dec. 14, 2015 for PCT/US2015/049908."

International search report dated Jan. 15, 2004 for PCT/US2003/026938.

International search report with written opinion dated Dec. 14, 2015 for PCT/US2015/049908.

Notice of allowance dated Feb. 26, 2013 for U.S. Appl. No. 13/648,986.

Notice of allowance dated Mar. 1, 2013 for U.S. Appl. No. 13/343,538.

Notice of allowance dated Apr. 15, 2015 for U.S. Appl. No. 12/532,630.

Notice of allowance dated Aug. 10, 2012 for U.S. Appl. No. 13/347,046.

Notice of Allowance dated Nov. 1, 2013 for U.S. Appl. No. 13/648,992.

Notice of Allowance dated Nov. 18, 2013 for U.S. Appl. No. 13/866,887.

(56) References Cited

OTHER PUBLICATIONS

Notice of Allowance dated Nov. 23, 2011 for U.S. Appl. No. 10/493,854.
Office action dated Jan. 17, 2012 for U.S. Appl. No. 12/532,630.
Office action dated Jan. 17, 2013 for U.S. Appl. No. 13/648,992.
Office action dated Jan. 24, 2014 for U.S. Appl. No. 13/735,864.
Office action dated Feb. 11, 2009 for U.S. Appl. No. 10/493,854.
Office action dated Feb. 26, 2008 for U.S. Appl. No. 10/493,854.
Office action dated Feb. 26, 2014 for U.S. Appl. No. 12/532,630.
Office action dated Mar. 13, 2013 for U.S. Appl. No. 12/532,630.
Office action dated Apr. 10, 2012 for U.S. Appl. No. 13/343,538.
Office action dated Apr. 10, 2013 for U.S. Appl. No. 12/532,630.
Office action dated Jun. 10, 2013 for U.S. Appl. No. 12/532,630.
Office action dated Jul. 12, 2011 for U.S. Appl. No. 10/493,854.
Office action dated Jul. 17, 2013 for U.S. Appl. No. 13/735,864.
Office action dated Jul. 23, 2013 for U.S. Appl. No. 13/648,992.
Office action dated Jul. 23, 2013 for U.S. Appl. No. 13/866,887.
Office action dated Aug. 20, 2010 for U.S. Appl. No. 10/493,854.
Office action dated Aug. 25, 2015 for U.S. Appl. No. 14/175,042.
Office action dated Sep. 14, 2011 for U.S. Appl. No. 10/493,854.
Office action dated Nov. 6, 2012 for U.S. Appl. No. 12/532,630.
Office action dated Nov. 6, 2015 for U.S. Appl. No. 14/801,850.
Office action dated Nov. 19, 2013 for U.S Appl. No. 12/532,630.
Office action dated Dec. 11, 2012 for U.S. Appl. No. 13/343,538.
Notice of allowance dated Oct. 25, 2017 for U.S. Appl. No. 14/537,814.
Office action dated Mar. 7, 2017 for U.S. Appl. No. 14/537,814.
EP15840142.2 Extended European Search Report dated Mar. 15, 2018.

INTRODUCER SHEATH WITH EMBOLIC PROTECTION

CROSS-REFERENCE TO RELATED APPLICATION

This application is a continuation of U.S. patent application Ser. No. 14/537,814, filed Nov. 10, 2014, now U.S. Pat. No. 9,877,821, which claims the benefit of U.S. Provisional Application No. 62/050,156, filed Sep. 14, 2014, the full disclosure of which is incorporated herein by reference.

BACKGROUND OF THE INVENTION

1. Field of the Invention

The present invention relates generally to medical devices and methods and more particularly to apparatus and methods for providing embolic protection to a patient's aortic arch vessels during cardiac surgery and interventional cardiology procedures.

Cerebral embolism is a known complication of cardiac surgery, cardiopulmonary bypass and catheter-based interventional cardiology and electrophysiology procedures. Embolic particles, which may include thrombus, atheroma, and lipids, may become dislodged by surgical or catheter manipulations and enter the bloodstream, embolizing in the brain or other vital organs downstream. Cerebral embolism can lead to neuropsychological deficits, stroke and even death.

Prevention of embolism would benefit patients and improve the outcome of many surgical procedures. Many current devices for preventing cerebral embolism may be less than ideal in various respects. For example, such current devices may involve multiple components and multiple steps, making the use of such devices cumbersome and even injury-prone for the patient. Also, when used with other catheter-based interventional tools, the patient's vasculature may need to be accessed at multiple points and through multiple paths. For example, a current embolic protection device may be advanced into the aortic arch through the descending aorta while other catheter-based interventional tools may then need to be advanced into or into proximity with the heart through other blood vessels including the vena cava, the right common carotid artery, and the left common carotid artery.

U.S. Patent Publ. 2013/0178891, commonly assigned herewith, describes an embolic protection device having embolic protection elements that are combined with an access sheath suitable advancing a diagnostic catheter. The embolic protection elements include an embolic filter slidably mounted on a distal portion of the sheath, a proximal stop for limiting the proximal movement of the embolic filter, and a distal stop for limiting the distal movement of the embolic filter. The filter comprises a porous mesh material defining a collection chamber for captured emboli and has a collapsed and a deployed configuration. The filter may be collapsed by an access sheath used with the catheter. An access sheath may comprise a tubular main body and an embolic filter mounted on the distal portion of the tubular main body. The embolic filter may revert into the central lumen of the sheath or may be constrained on the exterior of the sheath with a larger diameter outer tube.

While very effective for protecting the aortic branch vessels from emboli, the illustrated access sheath allows only a single catheter at a time to pass through the filter. Moreover, the sheath dimensions can limit the size of catheter which can be introduced which is a particular concern if a valvuloplasty catheter or prosthetic aortic or other valve is to be delivered over the aortic arch to the heart. Therefore, improved devices, systems, and methods for preventing embolism during cardiac procedures performed over the aortic arch that overcome at least some of the aforementioned short-comings are desired.

2. Description of the Background Art

U.S. Patent Publ. 2013/0178891 has been described above. Other devices for capturing or blocking emboli to prevent cerebral embolism are described in the following patent application and patent publications: U.S. Pub. No. 2010/0312268 to Belson, entitled "Embolic Protection Device"; U.S. Pub. No. 2004/0215167 to Belson, entitled "Embolic Protection Device"; U.S. Pub. No. 2003/0100940 to Yodfat, entitled "Implantable Intraluminal Protector Device and Method of Using Same for Stabilizing Atheromoas"; PCT Pub. No. WO/2004/019817 to Belson, entitled "Embolic Protection Device"; U.S. Pat. No. 6,537,297 to Tsugita et al., entitled "Methods of Protecting a Patient from Embolization During Surgery"; U.S. Pat. No. 6,499,487 to McKenzie et al., entitled "Implantable Cerebral Protection Device and Method of Use"; U.S. Pat. No. 6,371,935 to Macoviak et al., entitled "Aortic Catheter with Flow Divider and Methods for Preventing Cerebral Embolization"; U.S. Pat. No. 6,361,545 to Macoviak et al., entitled "Perfusion Filter Catheter"; U.S. Pat. No. 6,254,563 to Macoviak et al., entitled "Perfusion Shunt Apparatus and Method"; U.S. Pat. No. 6,139,517 to Macoviak et al., entitled "Perfusion Shunt Apparatus and Method"; and U.S. Pat. No. 5,769,819 to Barbut et al., entitled "Cannula with Associated Filter."

BRIEF SUMMARY OF THE INVENTION

The present invention provides methods, systems, and devices for collecting emboli and in particular for preventing the release of emboli into the cerebral vasculature during the performance of interventional procedures in a patient's aorta, including aortic valve replacement, aortic valve valvuloplasty, and the like, where there is a risk of emboli being released into the aortic side vessels, including the brachiocephalic artery, the left carotid artery, and the left subclavian artery. The present invention provides an embolic protection device and system which can be placed through the descending aorta and over the aortic arch to inhibit emboli release into the aortic side branch vessels while allowing simultaneous access to the aortic valve by at least two interventional and/or diagnostic catheters being introduced from the descending aorta, typically by conventional femoral artery access.

The embolic protection device will include both an embolic filter and an inner sheath connected to the embolic filter. The inner sheath is attached to or on a downstream portion of the embolic filter, where downstream refers to the direction towards the descending aorta and away from the heart and aortic arch. The inner sheath has a lumen and will provide a first access route to an interior of the embolic filter for introducing one diagnostic or interventional catheter at a time. At least one additional port will be formed in the embolic filter for introducing at least one additional catheter so that the additional or second catheter can be present within the interior of the embolic filter simultaneously with the initial or first catheter introduced through the sheath. The additional port will typically have an expandable diameter so it will remain generally closed when no catheter is present but will be able to open and to conform to catheters of different diameters as they are introduced therethrough into the interior of the embolic filter and typically onward to the aortic valve for performing an aortic intervention.

In a first specific aspect of the present invention an embolic protection device comprises an inner sheath having a lumen with a distal opening and an embolic filter. The embolic filter comprises a porous mesh material having a cylindrical outer wall which defines an interior which includes a collections chamber for capturing emboli. The filter has an open upstream end and a closed downstream end, where blood and emboli my enter through the open upstream end and deposit within the collection chamber which is at least partially defined by the closed downstream end. The filter will further have both a radially collapsed delivery configuration and a radially expanded configuration, and the outer wall will typically be configured to contact a blood vessel wall to direct blood flow through the upstream end and emboli into the collection chamber. The embolic filter will have at least a first port comprising an expandable opening configured to conform to an outer wall of a first catheter passing there through and a second port which is attached to the inner sheath to allow a second catheter to be advanced through the lumen of the inner sheath so that it can enter the interior of the embolic filter.

In specific embodiments of the embolic protection device of the present invention, at least one of the first port and the second port is formed in the closed downstream end of the embolic filter. Often, both the first and second ports will be formed in the closed downstream end, but in other embodiments at least one of the ports may be formed through the cylindrical outer wall of the porous mesh material, for example where the inner sheath may pass through a port or opening though the cylindrical outer wall at a location in an upstream direction from the closed downstream end of the filter.

In still other embodiments of the embolic protection device, the embolic filter further includes at least a first conical inner portion which defines the collection chamber between an inner surface of the outer cylindrical wall and an outer surface of the conical inner portion. In such embodiments, an apical end of the conical inner portion will be oriented towards the open upstream end of the embolic filter. Typically, the first port having an expandable opening will be formed at or in the apical end of the conical portion, in such embodiments, the conical portion will have a wide opening at its downstream end to facilitate entry of a diagnostic or interventional catheter through the expandable port. The expandable port may comprise a simple slit or duck-bill-like opening, or optionally may further comprise a resilient seal positioned within or over the port for conforming to a catheter as it passes through the port.

In still further embodiments, the embolic protection device may include a second conical inner portion which, together with the first conical inner portion, will define the collection chamber between the inner surface of the cylindrical outer wall and the outer surfaces of both the first and second conical inner portions. In such instances, the apical end of the second conical inner portion will be oriented towards the upstream end of the embolic filter, and typically the inner sheath is attached to the apical end of the second conical inner portion, more typically being attached so that an upstream end of the inner sheath will be positioned beyond the apical end of the second conical structure in the upstream direction.

In still other embodiments, a distal portion of the inner sheath may pass through the second port of the embolic filter and extend in an upstream direction some distance within the interior of cylindrical wall. In some cases, the inner sheath may be attached to the cylindrical wall or, in other cases, to a side wall of the first conical inner portion. In still other embodiments, the inner sheath may pass through a wall of the first conical inner portion so that the sheath enters the embolic filter through the open downstream end of the conical inner portion and then passes into the interior of the filter portion through the wall of the conical inner portion. A variety of other ways for attaching the inner sheath to the embolic filter described in more detail below.

The porous mesh material will typically be formed from an elastic or super elastic metal, such as nickel-titanium alloy, which can be preformed into its radially expanded configuration and then constrained into its radially collapsed delivery configuration, either by an external outer delivery sheath or by an internal stylet used to elongate the embolic filter. Other available materials for the porous mesh included knitted fabrics, woven fabrics, woven fibers, non-woven fibers, filaments, and wires having a pore size chosen to prevent emboli larger than a predetermined size from passing through the mesh. Other materials include other metals, polymer materials, plastically deformable materials, and the like. In the case of malleable and plastically deformable materials, further structure may be provided to radially expand and radially collapse the embolic filter before delivery and deployment. Typical pore sizes for the mesh materials are in the range from about 0.1 mm to about 1 mm, and the porous mesh material will typically be coated with an anti-thrombogenic coating. Radiopaque markers will be typically provided on the embolic filter and/or the inner sheath.

In a second aspect of the present invention, a method for advancing a catheter over an aortic arch having aortic side vessels comprises providing an embolic protection device including a cylindrical outer sleeve formed at least partly from a porous mesh and having an interior which defines a collection chamber for captured emboli. The embolic protection filter will have an open upstream end, a closed downstream end, a radially collapsed delivery configuration, and a radially expanded configuration for deployment within the aortic arch. The cylindrical outer sleeve is radially expanded so that the porous mesh covers the aortic side vessels and the upstream faces the heart to direct blood flow through the upstream end of the filter and emboli into the collection chamber. As a result, blood flowing into the aortic side vessels will pass through the porous mesh which will separate the emboli. After the filter is in position, a first catheter may be advanced from an arterial lumen downstream of the closed downstream end of the embolic protection filter through a first port therein. A second catheter may be advanced from the same or a different arterial lumen downstream of the closed downstream end of the embolic protection filter through a second port. In this way, at least two catheters may be simultaneously introduced into the interior of the filter and optionally beyond to the aortic valve in order to perform the desired aortic valve interventions. For example, a small catheter for delivering contrast media may be introduced through one of the ports while a second interventional catheter may be delivered through the other port. The contrast delivery catheter may be positioned within the filter to release contrast media, while the interventional catheter may be advanced out through the open upstream end of the filter in order to perform the desired intervention on the aortic valve.

In a first specific embodiment of the methods of the present invention, the embolic protection filter may further include a first conical inner structure formed through the cylindrical outer sleeve and having an apical end directed into the blood flow from the heart. The first port may be disposed at or near the apical end of the first conical inner structure where the availability of the enlarged downstream end of the conical port is particularly advantageous for receiving larger, interventional catheters therethrough.

In still other embodiments, a second inner sheath may be attached to the second port so that the second catheter may be advanced through a lumen of the inner sheath before passing through the second port. The inclusion of the inner sheath provides a number of advantages. As a first advantage, the inner sheath may be used to advance and position the embolic protection filter within the aortic arch. For example, the inner sheath may be used to advance the embolic protection filter through an outer delivery sheath that constrains the embolic protection filter and its radially collapsed configuration while it is being delivered. The embolic protection filter will typically be self-expanding, as described above, allowing it to radially expand and assume its deployed configuration as it is advanced beyond a distal end of the delivery sheath. Alternatively, a stylet may be positioned within the inner sheath and extend through the embolic protection filter to selectively elongate and radially collapse the embolic protection filter while it is being delivered. When using the stylet, the embolic protection filter may be radially expanded by proximally retracting the stylet relative to the filter to release the filter from radial constraint.

The embolic protection device will usually be self-supporting in the deployed condition. In other embodiments, however, the filter can include one or more "stent-like" support structures that may comprise, for example, a framework having one or more longitudinal struts or hoops that form a an outer surrounding and/or inner supporting lattice structure that assists in the expansion and wall apposition of the device. The hoops and struts may be made of a resilient metal and/or polymer material to make a self-expanding framework or a malleable or plastically deformable material to make a framework that can be expanded with an inflatable balloon or other expansion mechanism. Alternatively, the framework can be made of a shape-memory material that can be used to deploy and/or retract the embolic protection device.

The length of embolic protection device of the present invention should be sufficient to cover the aortic side vessels and to extend sufficiently into the ascending and descending regions of the aorta on both sides of the side vessels to assure that no emboli can bypass the filter. Beyond that requirement, the length of the device is not critical and may be constructed with the filter mesh structure and optionally the "stent-like" support structure made either longer or shorter without adversely affecting the performance of the product. In other alternate construction, the "stent" support structure need not be cylindrical can for example be made slightly conical with the wider end of the cone oriented toward the upstream direction.

The embolic protection device of the present invention may be retracted and withdrawn together with or after the catheters used to perform a diagnostic or interventional procedure at the end of the procedure. Optionally, the embolic protection device may include features to assist in retracting the device for retrieval from the vessel. In one embodiment, a conical guiding structure may be slidably attached to the catheter at the proximal end of the device, the purpose of which is to assist the embolic protection device in collapsing when a retrieval sheath is advanced along the conical guiding structure. In another embodiment, portions of the embolic protection device may be constructed with retraction members or retrieval wires that are configured like purse strings or lassos around the circumference of the device. A pull loop or other graspable structure near the downstream end of the embolic protection device may be connected to the retraction members by one or more connecting members.

In still further embodiments, the filter may contain one or more support structures or wires that provide longitudinal stiffness to the device to prevent compression or movement of the filter during the procedure. Such wires or structures may extend the full length of the device or only for a portion of its length and such wires or structures shall be either fixedly or slidably attached to the access sheath.

DETAILED DESCRIPTION OF THE INVENTION

Figure 1:
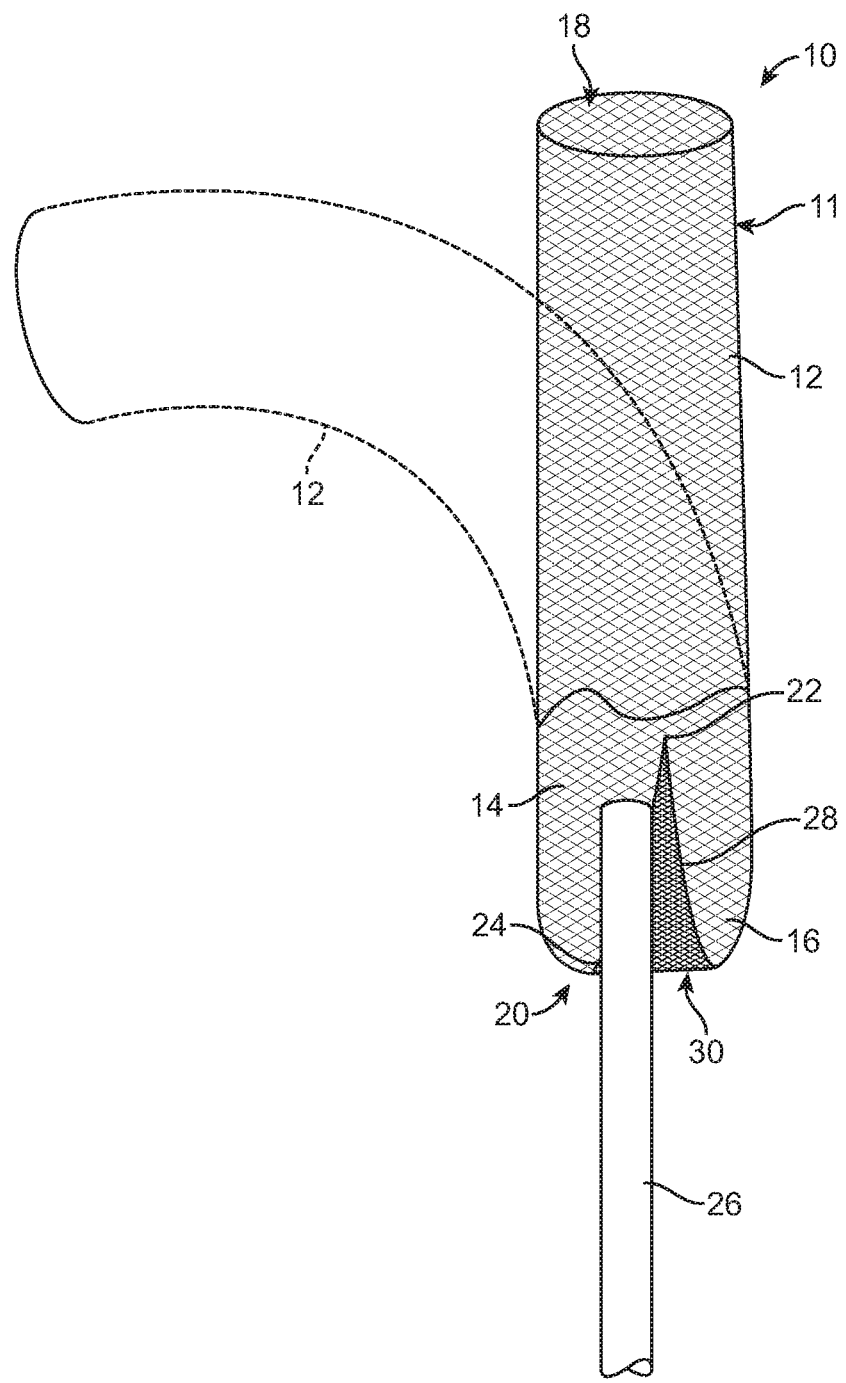
FIG. 1 illustrates an exemplary embodiment of an embolic protection device constructed in accordance with the principles of the present invention and including an embolic filter attached to an inner sheath through the wall of a conical inner portion. The filter element is shown in an axial configuration (full line) and a curved configuration (broken line).

Referring to FIG. 1, an embolic protection device 10 constructed in accordance with the principles of the present invention comprises an embolic filter component 11 including a cylindrical outer wall 12, an interior space or volume 14, a collection chamber 16, and a closed downstream end 20. An open upstream end 18 lies at the opposite end of the embolic filter component 11, where the terms downstream and upstream refer to the direction when the embolic filter 11 is placed in a patient's aorta. The open upstream 18 will be facing toward the heart and thus will be facing into blood flow from the heart. The downstream end 16 will be more remote from the heart and typically be disposed in the descending aorta, as will be described in more detail below with respect to FIG. 5A.

The cylindrical wall 12 will typically be a single layer or multiple layer porous mesh, usually formed from elastic wires, filaments, tapes, and most usually being formed from super elastic wires woven into a porous structure having a pore size typically in the range from 0.1 mm to 1 mm, usually from 0.1 mm to 0.2 mm.

In preferred constructions of the embolic filter 11 and cylindrical outer wall 12, the porous mesh will be elastic and pre-formed in a radially expanded configuration (so that it can be delivered in a radially constrained configuration and released from constraint to self-expand at the location of implantation in the target blood vessel) which is somewhat larger than a target blood vessel, typically larger than a target aorta, thus usually having a diameter in the range from 15 mm to 60 mm when unconstrained, more usually having a diameter in the range from 25 mm to 45 mm when unconstrained.

The embolic filter component 11 will also have a radially collapsed delivery configuration with a reduced diameter or profile kind of typically in the range from 2 mm to 6 mm, preferably in the range from 2 mm to 4 mm. The porous mesh construction is particularly suitable for axially elongating and radially collapsing the embolic filter component, and thus a preferred construction will be a woven mesh which is otherwise minimally supported or unsupported by any other structure. In other embodiments, however, it would be possible to provide either additional or internal support structures, such as stents, scaffolds, struts, grafts, coatings, circumscribing rings, or the like, depending on the desired specific mechanical characteristics. For the most part, however, such additional structural support will be unnecessary as the woven porous mesh structure when radially expanded will have sufficient hoop strength and column strength to both deploy and be maintained within the aorta arch, as described in more detail below.

The embolic filter component 11 of the embolic protection device 10 will also include at least a first port and a second port to allow catheter access from the outside of the embolic filter component to the inside of the embolic filter component. Often, the first port and the second port will be located on or near the closed distal end 20 of the embolic filter component. In other instances, either the first port, the second port or both the first and second ports, will be formed through the side wall 12 of the embolic filter component 10. Various specific implementations are illustrated in FIGS. 2A-2F discussed here and after.

In FIG. 1, the first port 22 is formed in a first conical inner portion 28 located at the closed downstream end 20 of the embolic filtered component 11. The first conical inner portion 28 advantageously defines the collection chamber 16 immediately above the closed downstream end 20 of the embolic filter component 11 and elevates the port 22 above the bottom of the collection chamber. In this way, emboli will collect in the collection chamber 16 at the base of the conical inner portion 28, leaving the port itself free from collected emboli and reducing the chance that such emboli will pass through the port as catheters are introduced and removed there through.

In FIG. 1, the second port 24 is conveniently formed in a side wall of the first conical inner portion 28, and the inner sheath 26 is disposed within and secured to the second port. Thus, in this embodiment, catheter access through the second port 24 is achieved by passing the catheter through a lumen of the inner sheath 26. Both the first port 22 and then the inner sheath 26 open into the interior 14 of the embolic filter component 11, with the point of entry being raised above the bottom of the collection chamber 16 to reduce the risk of emboli accidently passing through either port. The first port 22 will be expandable so that, in the absence of a catheter passing there through, the port will be closed and emboli passing into the emboli filter component 11 will not be able to pass through the port. Interventional or other catheters (not pictured in FIG. 1) may, however, be passed through the first port 22 by entering through the wide opening 30 at the base of the first conical inner portion 28 and then passing through the port 22 as the catheter advances into the tapered region of the conical inner portion. A second catheter may be passed through the lumen of the inner sheath 26 in a generally conventional manner. While the lumen of the inner sheath 26 is open and thus may allow entry of embolic material, inner sheath 26 provides a closed path to its external entry port, typically through an introducer sheath into the parent patient's femoral artery, so any emboli which enter the sheath will not be released into the patient's arterial circulation.

As shown in FIG. 1, the cylindrical side wall 12 of the embolic filter component 11 will typically be straight in its unconstrained or "shelf" condition. When placed in the aortic arch or other constraint, however, the cylindrical wall 12 may be curved, e.g. as shown in broken line in FIG. 1. Thus, after deployment in the aortic arch, the outer surface of the cylindrical wall can expand into and conform to an inner wall of the aortic arch in order to provide the desired filtering of the aortic side vessels.

Figure 2A:
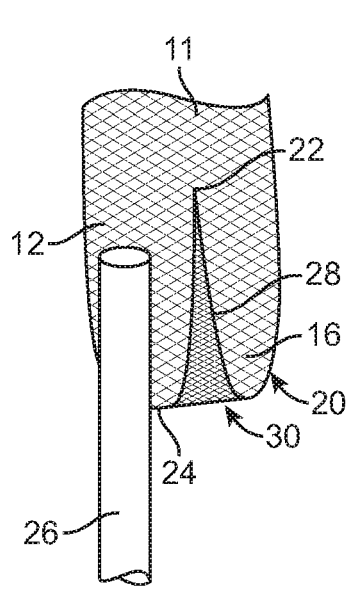
FIGS. 2A through 2G illustrate alternative constructions for the attachment of the inner lumen to the embolic filter of the embolic protection device of FIG. 1.

Referring now to FIGS. 2A-2G, the downstream half of the embolic filter component 11 may have a wide variety of configurations to provide the required first and second ports. As shown in FIG. 2A, the inner sheath 26 may be passed through the closed downstream end 20 of the embolic filter component 11 at a location spaced laterally or radially from the base of the first conical inner portion 28. Instead of being attached to the side of the first conical inner portion 28, as with the embodiment of FIG. 1, a distal region of the inner sheath 26 may be attached to an inner surface of the side wall 12.

Figure 2B:
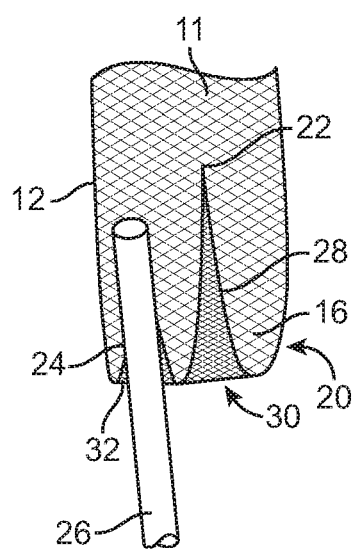

Referring now to FIG. 2B, the second port 24 may be formed in an apical region of a second conical inner portion 32. Unlike the first conical inner portion 28, however, the access sheath 26 will usually be fixedly or permanently attached to the port 24. As shown in FIG. 2B, the open distal end of the access sheath 26 extends well beyond the port 24. In other embodiments, however, the height or length of the second conical inner portion 32 could be attached directly to the second port 24.

Figure 2C:
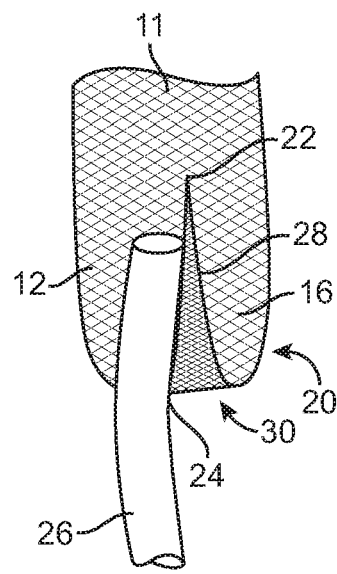

Referring now to FIG. 2C, in a fourth specific embodiment, the inner sheath 26 may be passed through the closed downstream end 20 at location immediately adjacent to the base of the first conical inner portion 28. A distal region of the inner sheath 26 may then be attached to an outer wall portion of the first conical inner portion, as illustrated.

Figure 2D:
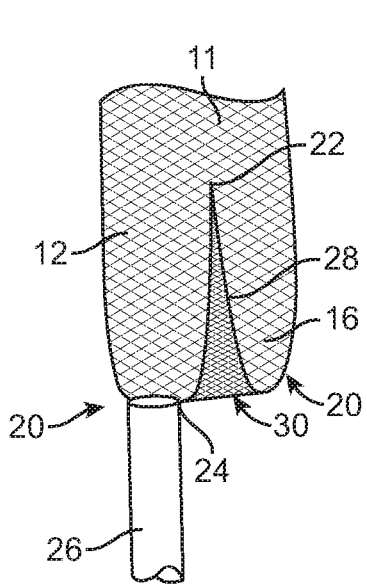

In a still further embodiment, as illustrated in FIG. 2D, a distal of the inner sheath 26 may be attached directly to a second port 24 formed in the closed downstream end 20 of the embolic filter component 11.

Figure 2E:
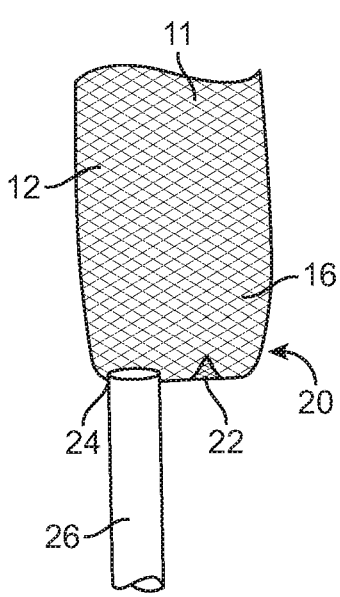

In another embodiment, as illustrated in FIG. 2E, the inner sheath 26 is attached as shown in FIG. 2D and the first port 22 is also formed directly in the closed downstream end 20 of the embolic filter component 11. The port 22 may extend minimally or not at all over a base of the closed downstream end 20.

Figure 2F:
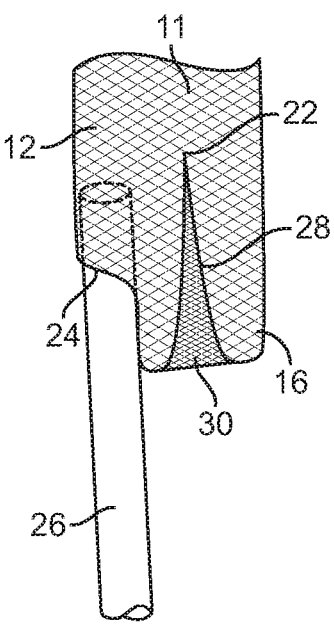

In a still further embodiment of the inner sheath attachment detail, as shown in FIG. 2F, the inner sheath 26 may enter through a port 24 formed in the side wall 12 of the embolic filter component 11. Other aspects of the embolic filter component 11 remain the same as described in, for example, FIG. 2A above.

Figure 2G:
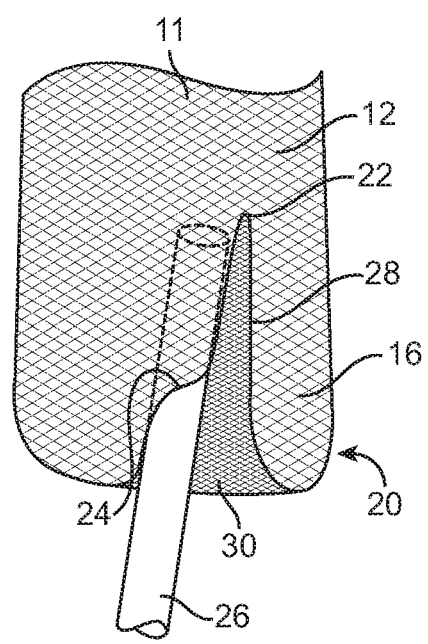

As a final exemplary embodiment of the inner sheath attachment detail as illustrated in FIG. 2G, the inner sheath 26 may enter the wide downstream end 30 of the inner conical portion 28. A port 24 is located in the region between the closed downstream end 20 and the apical end of the conical inner portion. A distal region of the inner sheath 26 may then be attached to an outer wall portion of the first conical inner portion 28. Having the distal region of the inner sheath 26 pass through the inner wall of the conical inner portion provides a particularly secure connection between the sheath and the filter.

Figure 3:
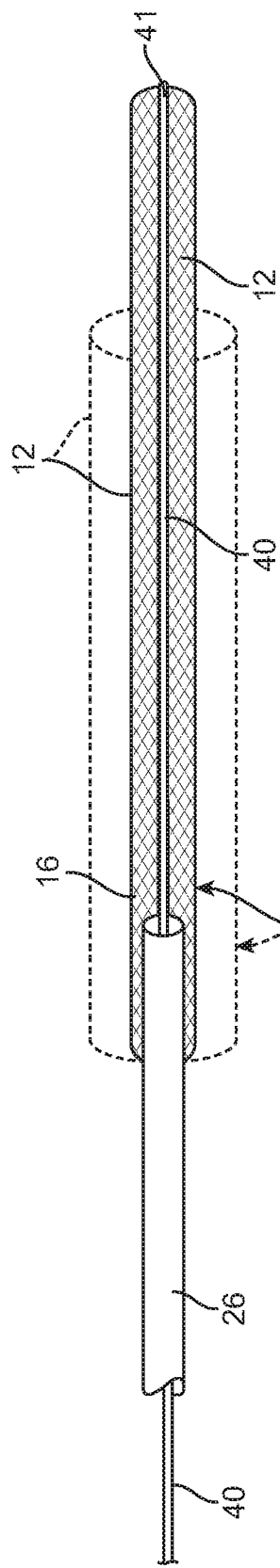
FIG. 3 illustrates use of a stylet for axially elongating the embolic filter of the embolic protection device of FIG. 1 to reduce the filter diameter to a radially collapsed diameter for delivery.

Referring now to FIG. 3, the embolic filter component 11 may be configured to have a reduced diameter for delivery by inserting a stylet 40 into the interior 16 of the embolic filter component 11 so that a distal tip 41 of the stylet engages the downstream end of the embolic filter and axially elongates the filter in order to radially collapse the diameter, typically to a diameter in the ranges as set forth above. As shown in FIG. 3, the cylindrical wall 12 of the embolic filter component 11 is shifted from an unconstrained diameter, shown in broken line, to the radially collapsed diameter, as shown in full line. In a further embodiment, to enable a more secure connection, the stylet may engage the filter at multiple locations along its length in addition to at the distal tip 41.

Figure 4:
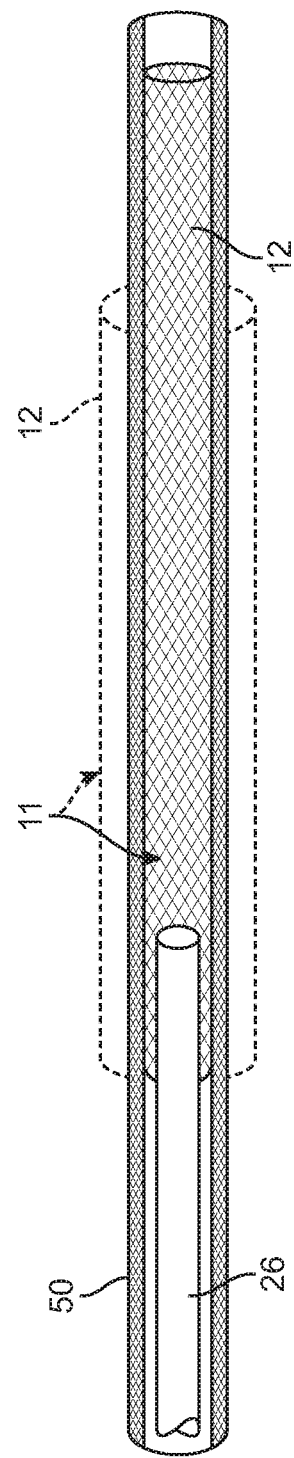
FIG. 4 illustrates use of an outer sheath for a radially constraining the embolic filter of the embolic protection device of FIG. 1 for delivery.

An alternative structure for radially collapsing the embolic filter component 11 is shown in FIG. 4 where an outer delivery sheath 50 is placed over the exterior of the cylindrical outer wall 12 of the embolic filter component 11 in order to axially elongate and radially reduce the filter, as shown in full line. By retracting the outer delivery sheath 50 from over the embolic filter component 11, the filter component will reassume the radially expanded configuration, as shown in broken line.

Figure 5A:
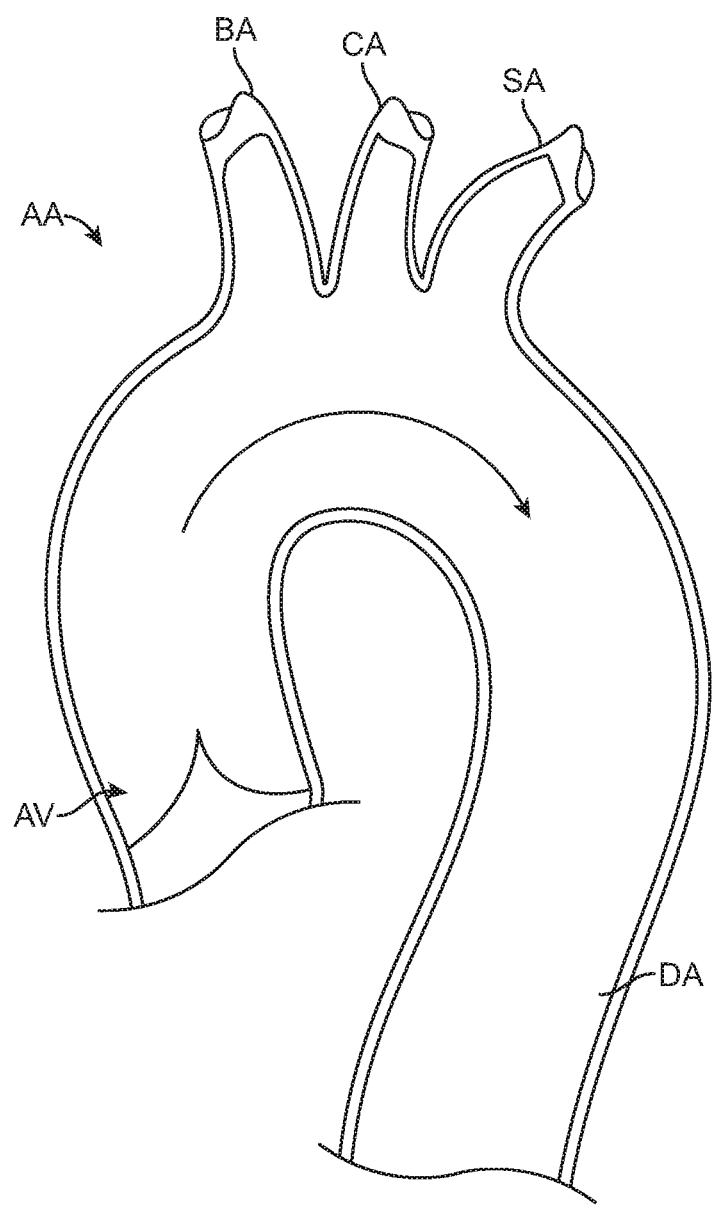
FIGS. 5A through 5E show an exemplary embolic filter deployment protocol using the embolic protection device and stylet of FIGS. 1 and 3.

Referring now to FIG. 5A through 5E, delivering of an embolic filter component 11 in accordance with the principles of the present invention will be described. The aortic anatomy as illustrated in FIG. 5A where an aortic arch AA receives blood flow from an aortic valve AV in the direction of the arrow so that the blood flows down the descending aorta DA. The brachiocephalic artery BA, the left carotid artery CA, and the left subclavian artery, referred to herein collectively as the "aortic side vessels," all branch from the aortic arch and a primary purpose of the present invention is to prevent emboli released from the aortic valve from entering these aortic side vessels during the performance of any aortic valve intervention.

Figure 5B:
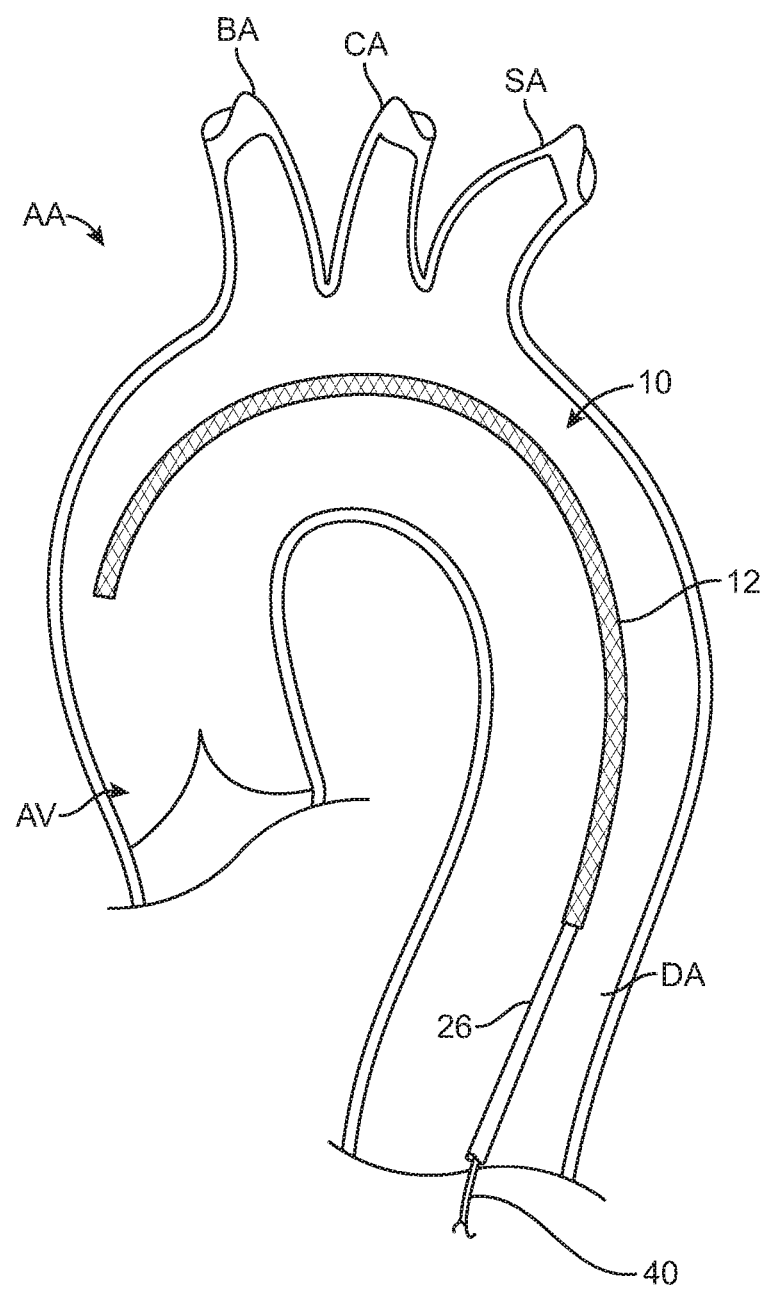
Figure 5C:
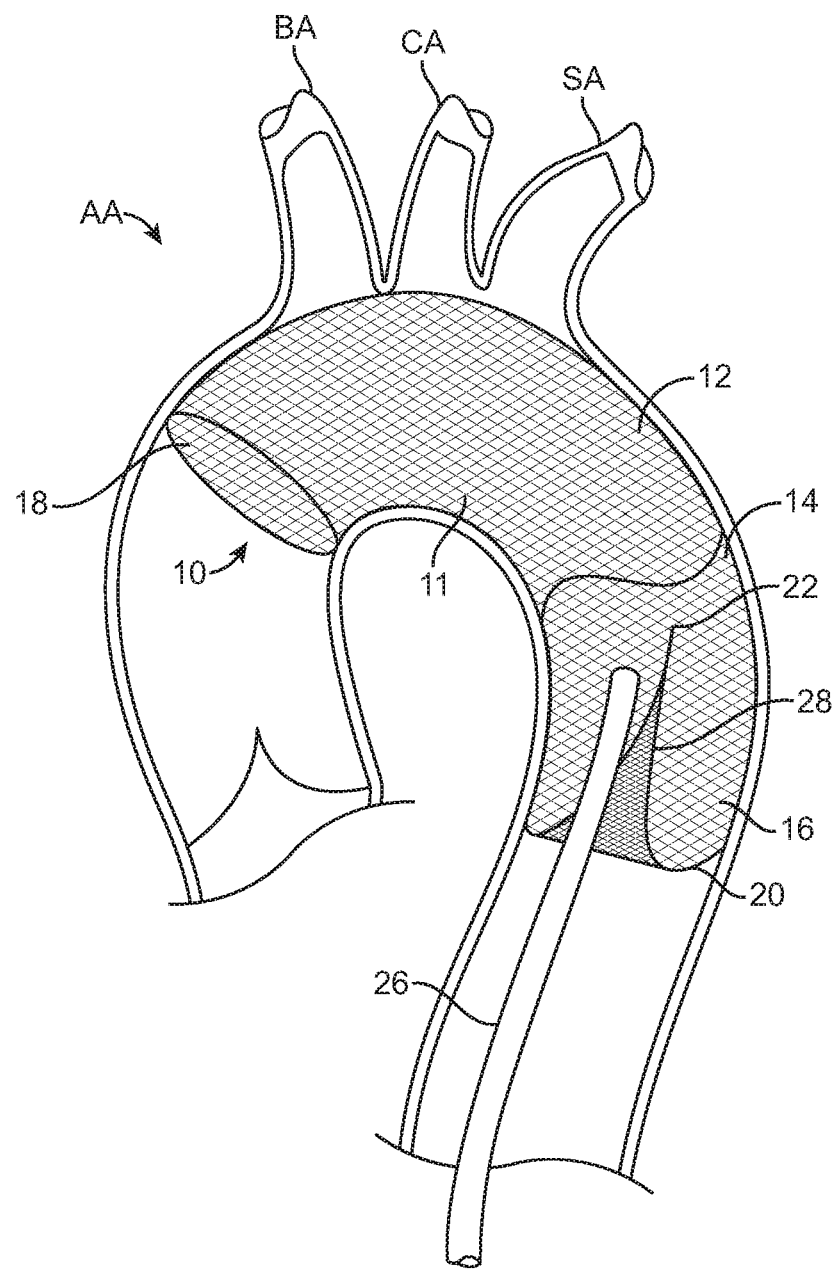

As shown in FIG. 5B, the embolic protection device 10 of FIG. 1 may be advanced using a stylet 40, as illustrated in FIG. 3. Once in place with the cylindrical outer wall 12 disposed over the aortic arch, the stylet 40 may be removed allowing the cylindrical outer wall 12 to radially expand to cover at least the entries into the aortic side vessels, as shown in FIG. 5C. Once the filter is deployed, the open upstream end 18 of the embolic filter component 11 is disposed over the aortic valve AV to provide catheter access for one more interventional catheters. It will be appreciated that this open upstream end 18, while allowing relatively unfettered access for the intervention, will also receive emboli released by the intervention into the interior 14 of the embolic filter component 11. The presence of the porous mesh or other filter structure of the embolic filter component 11 over the entries to the aortic side vessels will divert and prevent emboli from entering these vessels.

Figure 5D:
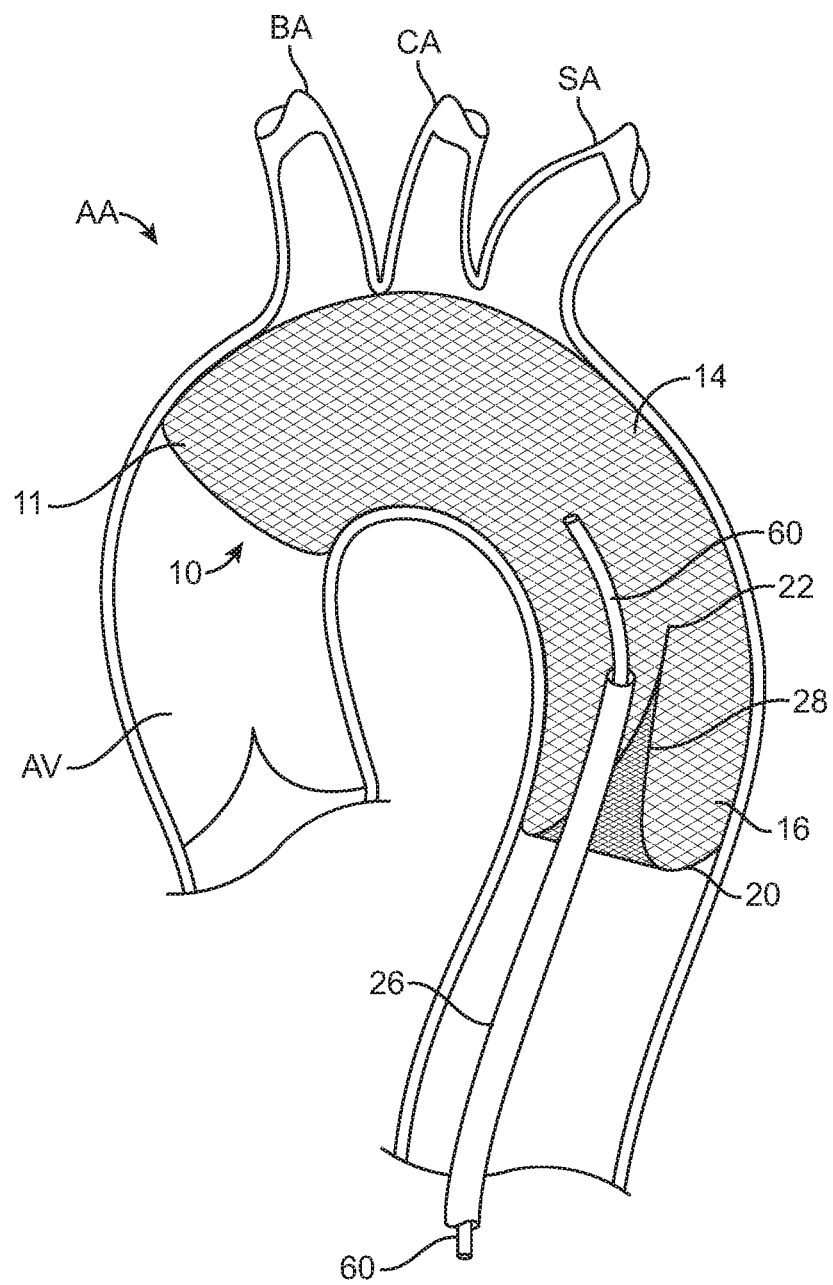

As shown in FIG. 5D, a first catheter, such as a contrast delivery catheter 60, may be introduced through a lumen of the inner sheath 26 so that it enters into the interior 14 of the embolic filter component 11, typically at a location close to the side branch vessels.

Figure 5E:
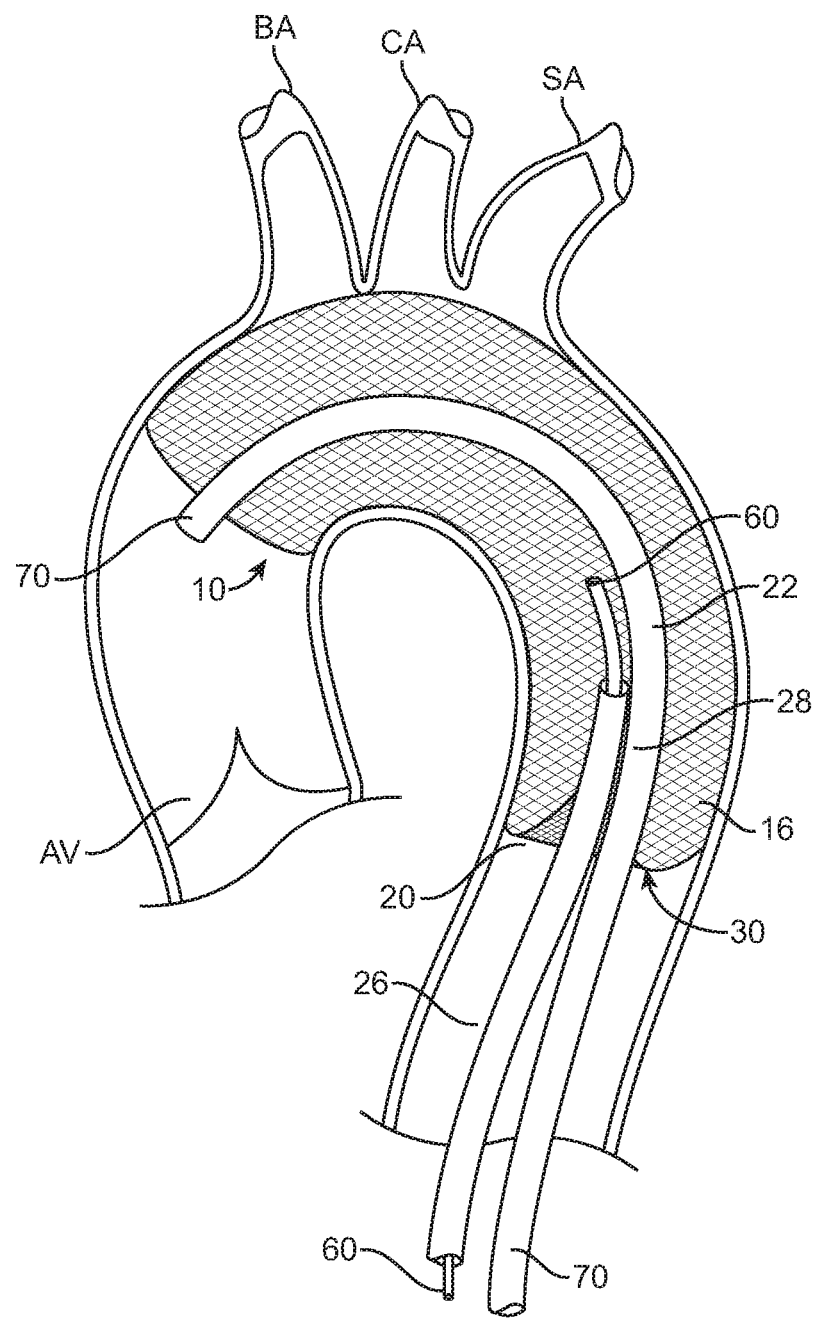

As shown in FIG. 5E, a second catheter 70, typically an interventional catheter such as a valve delivery catheter, an annuloplasty catheter, or the like, may then be introduced through the second port 22 by passing a distal end of the catheter through the wide opening 30 at the base of the first conical inner portion 28 so that the catheter 70 passes through and opens the first port 22. The first port 22 will preferably expand and conform over the exterior of the second catheter 70 so that the risk of emboli passing through the second port is minimized or eliminated. Upon removal of the second catheter 70, the access port 22 will close to prevent emboli from passing through it.

The methods and apparatus of the present invention are not limited to any particular interventional or diagnostic catheters or the performance of any particular interventional or diagnostic procedures. Instead, the access ports 22 and 24 can provide for introduction of a wide variety of catheters and tools for performing a number of desired interventions on the aortic valve or anywhere in ascending aorta therein. Further alternative embodiments may include more than two access ports, at least one of which will be expandable as with port 22 and at least one of which will be fixedly attached to an access sheath as with port 24. Additional expandable ports may also include additional inner conical portions.

What is claimed is:

1. An embolic protection device, said device comprising:
   a cylindrical porous mesh filter having an open distal end, a closed proximal end, an interior including a collection chamber, a radially collapsed delivery configuration, and a radially expanded configuration; and
   a sheath having a distal end, a proximal end, and an inner lumen extending from the proximal end to the distal end, said distal end of the sheath being fixedly attached to a proximal end of the cylindrical porous mesh filter and said inner lumen being configured to allow passage of a catheter therethrough;
   wherein the closed proximal end of the cylindrical porous mesh filter is fixedly attached to the distal end of the sheath and has a radially expandable port configured to receive catheters of different diameters therethrough; and
   wherein a first catheter may be introduced into the interior of the cylindrical porous mesh filter through the inner lumen of the sheath and a second catheter may be introduced into the interior of the cylindrical porous mesh filter though the expandable port.

2. An embolic protection device as in claim 1, wherein the radially expandable port is disposed at an apical end of a conical inner portion of the closed proximal end of the cylindrical porous mesh filter.

3. An embolic protection device as in claim 1, wherein the distal end of the sheath is fixedly attached to a port on the proximal end of the cylindrical porous mesh filter.

4. An embolic protection device as in claim 2, wherein the conical inner portion defines the collection chamber between an inner surface of a cylindrical outer wall and an outer surface of the conical inner portion, wherein the apical end of the conical inner portion is oriented toward the open upstream end of the embolic filter.

5. An embolic protection device 4, wherein the conical inner portion is positioned inside the cylindrical outer wall and has a wider proximal end joined to a proximal of the cylindrical outer cylindrical outer wall to form the closed proximal end.

6. An embolic protection device as in claim 4, wherein the open distal end of the cylindrical porous mesh filter is configured to allow blood to flow between the conical inner portion and the cylindrical outer portion, with a space between the conical inner portion and the cylindrical outer portion defining the collection chamber for captured emboli.

7. An embolic protection device as in claim 1, wherein the cylindrical porous mesh filter self-expands into the expanded configuration when the filter is in the deployed configuration.

8. An embolic protection device as in claim 7, wherein the cylindrical porous mesh filter comprises a fabric of knitted, woven, or nonwoven fibers, filaments, or wires having a pore size chosen to prevent emboli over a predetermined size from passing through.

9. An embolic protection device as in claim 7, wherein the cylindrical porous mesh filter is made of a resilient metal, polymer material, a malleable material, a plastically deformable material, a shape-memory material, or combinations thereof.

10. An embolic protection device as in claim 1, wherein the cylindrical porous mesh filter has an anti-thrombogenic coating on its surface.

11. An embolic protection device as in claim 1, wherein the cylindrical porous mesh filter has a pore size in the range of about 1 mm to about 0.1 mm.

12. An embolic protection device as in claim 1, further comprising a resilient seal positioned within the expandable port for forming a seal around a catheter passing through the expandable port.

13. An embolic protection system comprising:
an embolic protection device as in claim 1; and
a delivery sheath having a lumen there through configured to restrain the embolic filter in its radially collapsed delivery configuration when the embolic filter is there within, wherein the embolic filter deploys into its radially expanded configuration when the embolic filter is advanced out of the outer delivery sheath.

14. An embolic protection system comprising:
an embolic protection device as in claim 1; and
a stylet configured to be advanced through the sheath lumen and the embolic filter to elongate the embolic filter to assume its radially collapsed delivery configuration, wherein the embolic filter deploys into its radially expanded configuration when the stylet is removed from the embolic filter.

15. A method for advancing a catheter over a patient's aortic arch having aortic side vessels, said method comprising:
providing an embolic protection device as in claim 1;
advancing the sheath through the patient's aorta to position the cylindrical porous mesh filter over the aortic arch;
radially expanding the cylindrical porous mesh filter within the aortic arch to cover the aortic side vessels with the open distal end facing the patient's heart to direct blood flow through the upstream end and emboli into the collection chamber, wherein blood free from emboli flows through the porous mesh into the aortic side vessels;
advancing the first catheter through the inner lumen of the sheath, through the interior of the cylindrical porous mesh filter, and toward the heart; and
advancing the second catheter through the though the expandable port, through the interior of the cylindrical porous mesh filter, and toward the heart.

16. A method as in claim 15, further comprising performing a first diagnostic or interventional procedure with the first catheter and performing a second diagnostic or interventional procedure with the second catheter.

17. A method as in claim 15, wherein the sheath is used to advance the cylindrical porous mesh filter through a delivery sheath that constrains the embolic protection device in its radially collapsed configuration while it is being delivered.

18. A method as in claim 17, wherein radially expanding the cylindrical porous mesh filter comprises proximally retracting the delivery sheath relative to the embolic protection device to release the embolic protection device from radial constraint.

19. A method as in claim 15, further comprising performing an interventional procedure with the first catheter positioned through the first port and introducing contrast media through a second catheter positioned through the inner sheath and second port while the interventional procedure is being performed.

20. A method as in claim 19, wherein the interventional procedure is delivery of a prosthetic aortic valve.

* * * * *